United States Patent [19]
White

[11] 3,987,094
[45] Oct. 19, 1976

[54] PREPARING CARBOXYLIC ACIDS FROM GLYCIDONITRILES
[75] Inventor: David R. White, Kalamazoo, Mich.
[73] Assignee: The Upjohn Company, Kalamazoo, Mich.
[22] Filed: Dec. 10, 1974
[21] Appl. No.: 531,432

[52] U.S. Cl. .................. 260/515 R; 260/239 BA; 260/287 R; 260/293.88; 260/295 R; 260/326.4; 260/326.11 R; 260/326.13 R; 260/332.2 A; 260/397.1; 260/413; 260/465 D; 260/465.4; 260/479 R; 260/488 R; 260/514 R; 260/514 H; 260/514 G; 260/514 L; 260/515 P; 260/518 R; 260/520 R; 260/521 R; 260/526 N; 260/534 R; 260/540
[51] Int. Cl.² .................. C07C 51/02; C07C 51/00
[58] Field of Search ............ 260/515 R, 540, 465.4, 260/526 R

[56] References Cited
UNITED STATES PATENTS
2,266,771  12/1941  Lange et al. ............... 260/465.4
2,764,608  9/1956  Blair ........................ 260/465 D FOREIGN PATENTS OR APPLICATIONS
1,560,450  3/1969  France OTHER PUBLICATIONS
Deakin et al., J. Chem. Soc., 97, (1910), pp. 1968–1978.
Nowak, J. Org. Chem., 28, (1963), pp. 1182–1187.
Morrison et al., Organic Chemistry, 2nd Ed., (1966), pp. 582–583.
Malinouskii, Epoxides and Their Derivatives, (1965), pp. 188–192.

Primary Examiner—Lorraine A. Weinberger
Assistant Examiner—Michael Shippen
Attorney, Agent, or Firm—John T. Reynolds

[57] ABSTRACT

Process for preparing carboxylic acids by (1) reacting a glycidonitrile with a carboxylic acid halide in the presence of a catalytic amount of a tertiary amine or acid salt thereof to form a 2-acyloxy-3-halo-propionitrile, (2) dehydrohalogenating the halogenated acylate from step (1) to form the acyloxy acrylonitrile intermediate (enol-acylate) (3) hydrolyzing the enol-acylate from step (2) with aqueous base to form the carboxylic acid salt, and (4) acidifying the carboxylic acid salt with acid to form the carboxylic acid. Salts of persulfate and hypochlorite ions can be added to destroy cyanide ion. The process can be used to prepare a wide variety of carboxylic acids, e.g., 2-(4'-isobutylphenyl)propionic acid, now known generally as ibuprofen, a highly active anti-inflammatory drug.

13 Claims, No Drawings 3,987,094

PREPARING CARBOXYLIC ACIDS FROM GLYCIDONITRILES

INTRODUCTION

This invention relates to processes for preparing carboxylic acids. More particularly, this invention provides an improved process for preparing carboxylic acids from glycidonitriles through enol acylate intermediate formation via a combined halogenation-acylation treatment of the glycidonitrile starting material.

BACKGROUND OF THE INVENTION

Prior art carboxylic acid syntheses from aromatic ketones by the addition of hydrogen cyanide such as that disclosed by Eliel et al., in Organic Syntheses, 33, 7 (1953) involve a reversible step with an unfavorable equilibrium as well as a reduction step.

More recently, applications have been filed disclosing and claiming a process for preparing carboxylic acids by reacting glycidonitriles with a Lewis acid having a non-nucleophilic anion, i.e., an ionic Lewis acid, to form the 2-oxo-propionitrile, which is then hydrolyzed to the carboxylate salt with a strong base, and the salt is converted to the carboxylic acid with a strong acid. That process has the advantage of involving only three steps, but that process generates hydrogen cyanide gas when intermediates therein dimerize, which gas must be removed.

Also, applications have been filed disclosing and claiming a process for preparing carboxylic acids from glycidonitriles through enol acylates via a hydrohalogenation-acylation-dehydrohalogenation procedure, involving the use of hydrogen halide to effect halogenation and opening of the oxirane ring of the glycidonitrile starting material to form the 3-halo-2-hydroxy-propionitrile, acylation and dehydrohalogenation of the 3-halo-2-hydroxypropionitrile to form the enol-acylate (2-acyloxy acrylonitrile), followed by hydrolysis of the enol acylate with base to form the carboxylate salt, which salt is converted to the carboxylic acid with acid. This process uses more steps than the ionic Lewis acid process referred to above but permits the production of carboxylic acid from glycidonitriles in a process wherein the cyanide ion derived from the glycidonitrile is converted to an alkali metal cyanide which remains dissolved or suspended in the reaction mixture vessel to which can be added cyanide ion destroying substances.

However, in that process the hydrohalogenation, the acylation and the dehydrohalogenation are done in a sequence of steps which requires the use of relatively dilute solutions of the reactants and the use of large quantities of pyridine in the acylation-dehydrohalogenation step.

However, those in the art of process development continue to search for more efficient processes for making carboxylic acids.

OBJECT OF THE INVENTION

It is an object of this invention to provide an improved process for preparing carboxylic acids from glycidonitriles through enol-acylate intermediates.

It is a further object of this invention to provide a process for preparing carboxylic acids from glycidonitriles via a combined hydrohalogenation-acylation procedure.

It is another object of this invention to provide a process for preparing carboxylic acids from glycidonitriles via a hydrohalogenation-acylation-dehydrohalogenation procedure which saves on the amount of chemical reactants which must be used in the process.

Other objects, aspects and advantages of this invention will become apparent to those skilled in this art from reading the remaining specification and the claims which follow:

SUMMARY OF THE INVENTION

Briefly, by the process of this invention (1) a glycidonitrile is reacted with a carboxylic acid halide in the presence of a catalytic amount of a tertiary amine or a tertiary amine acid salt, in an amount and for a time sufficient to convert the glycidonitrile to a 2-acyloxy-3-halo-propionitrile, (2) the acylated-halopropionitrile from step (1) is dehydrohalogenated to form the 2-acyloxy acrylonitrile (enol acylate), (3) the enol acylate from step (2) is hydrolyzed with an aqueous alkali metal base to form the alkali metal salt of the carboxylic acid which is treated with a strong acid to form the carboxylic acid. In the process, the cyanide content of the reaction mixture can be destroyed by adding an alkali metal, alkaline earth metal or an ammonium salt of persulfate or hypochlorite ions in an amount sufficient to destroy cyanide ions therein, after the addition of the aqueous alkali metal base.

DETAILED DESCRIPTION OF THE INVENTION

More specifically, this invention provides a process for the production of a carboxylic acid of the formula

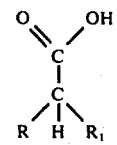

wherein
R, when taken separately, represents hydrogen or an aliphatic, alicyclic, aromatic or heterocyclic group,
R₁, when taken separately, represents an aliphatic, alicyclic, aromatic or heterocyclic group, and
R and R₁, when taken together and connected, represent an alicyclic or heterocyclic group, which comprises
1. treating a glycidonitrile of the formula

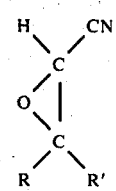

wherein R and R₁ have the meaning given hereinabove, with a carboxylic acid halide of the formula

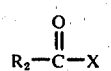

wherein

denotes the carboxylic acyl group having from 1 to 18 carbon atoms, and X is chlorine, bromine or iodine, in the presence of a catalytic amount of a tertiary amine or an acid salt thereof in an amount and for a time sufficient to form a 2-acyloxy-3-halo-propionitrile acylate of the formula

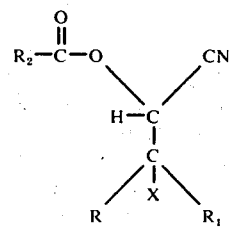

IV wherein R, $R_1$ and X are as defined above and $R_2C(O)$- is the residue of the carboxylic acyl group;

2. dehydrohalogenating the 2-acyloxy-3-halopropionitrile from step (1) with a base, preferably with a tertiary amine to form the acyloxy acrylonitrile, i.e., the (enol acylate) of the formula

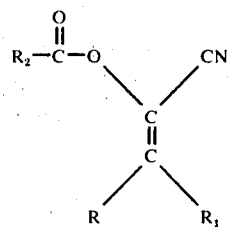

V wherein R, $R_1$ and $R_2$ are as defined above;

3. hydrolyzing the enol-acylate from step (2) with an aqueous alkali metal base to form an alkali metal salt of a carboxylic acid of the formula

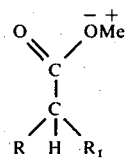

VI wherein R and $R_1$ are as defined above and $\overset{+}{Me}$ is the alkali metal cation from the base and is preferably a sodium, potassium or lithium cations, and 4. acidifying the alkali metal salt of the carboxylic acid from step (3) with an acid strong enough to form the corresponding free carboxylic acid (1).

Included among the aliphatic, alicyclic and aromatic groups which R and $R_1$ can each represent when taken separately are, for example, alkyl (including saturated and unsaturated, straight and branched chain alkyl and cycloalkyl) and aryl (including alkaryl and aralkyl) radicals, such as methyl, ethyl, propyl, isopropyl, n-butyl, sec. butyl, tert. butyl, amyl, hexyl, heptyl, octyl, decyl, dodecyl, octadecyl, vinyl, allyl, methallyl, butenyl, pentenyl, hexenyl, heptenyl, octenyl, ethynyl, propynyl, butynyl, pentynyl hexynyl, heptynyl, octynyl and isomeric forms thereof, cyclobutyl, cyclopentyl, cyclohexyl, 1-cyclohexenyl, methylcyclohexyl, cycloheptyl, cyclooctyl, cyclodecyl, cycloundecyl, cyclododecyl, cyclopentadecyl, phenyl, tolyl, xylyl, benzyl, phenethyl, phenylpropyl, benzhydryl, naphthylmethyl, o-carboxylbenzyl, and the like, as well as fused and bridged ring structures, such indenyl, naphthyl, acenaphtyl, phenanthryl, cyclopentanopolyhydrophenanthryl, adamantanyl, bicyclo[3:1:1]heptyl, bicyclo[2:2:2] octyl and the like; all of which can either be unsubstituted or substituted with one or more non-interfering substituents, such as hydroxyl derivatives, for example, alkoxy such as methoxy, ethoxy, propoxy, butoxy, and the like; acyloxy, such as acetoxy, propionoxy, butyroxy and the like; nitro groups; amino groups; alkylamino groups, such as methylamino, ethylamino, dimethylamino and the like; halogens, such as fluorine, chlorine, or bromine; carbonyl derivatives such as enol ethers and ketals; and the like.

Included among the heterocyclic groups which R and $R_1$ can represent are substituted and unsubstituted azabicycloalkane groups such as azabicyclo[3:2:2]octyl and azabicyclo[3:2:1] nonyl and the like, furfuryl groups, tetrahydrofurfuryl groups, piperidyl groups, pyrrolidyl groups, pyridyl groups, thiophene groups, alkaloid nuclei groupings containing for example indole, dihydroindole, quinolidine, quinthio groups and the like.

Included among the alicyclic and heterocyclic groups in which $R_1$ and $R_2$ when taken together and connected can represent, are cyclopropyl, cyclobutyl, cyclohexyl, dicyclohexyl, cyclodecyl, cyclododecyl, cyclopentadecyl, and the like; piperidyl, pyrrolidyl, and the like; fused ring systems such as cyclopentanopolyhydrophenanthranyl, indanyl, indenyl, and the like, bridged ring systems such as adamantyl, bicyclo[2:2:1]heptyl, bicyclo[2:2:2]octyl, bicyclo[3:2:2]nonyl, azabicycloalkyls, and the like, all of which can be substituted by non-interfering substituents such as those hereinbefore named.

The starting glycidonitriles of formula II are either known in the art or can be prepared from known ketones and aldehydes by a Darzens condensation, for example in accordance with the procedure disclosed by V. F. Martynov and A. V. Schelkunov, J. Gen. Chem. USSR 27, 1271–3 (1957). In preparing the necessary starting materials, a ketone or aldehyde of formula VII;

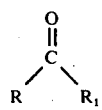

VII wherein R and $R_1$ have the same meanings given above, is reacted with chloroacetonitrile in the presence of a strong base such as sodium methoxide, potassium t-butoxide, sodium t-amylate and the like. The reaction is carried out in a non-polar aprotic solvent such as xylene, toluene, hexanes, petroleum ethers and the like, preferably at a relatively low temperature, such as from about −10° to about +10° C., for a period of from about 1 to 5 hours. In our preferred procedure for making glycidonitrile starting materials we use sodium hydroxide in a mixture of dimethylformamide and toluene. The glycidonitrile (II) thus obtained is recovered and purified by conventional methods, for example, by distillation under reduced pressure. See Tetrahedron Letters, (1970), pp. 2947–2950 for other uses of glycidonitriles.

The process of this invention is preferred for making carboxylic acid products where R is an aromatic, including alkylaryl radicals, and $R_1$ is aliphatic. For example the above described and herein after claimed process has been adapted for the production of 2-(4'-isobutylphenyl)propionic acid, now known generically as ibuprofen. Such preferred process can be described as including the following steps:

1. treating 4-isobutylphenylglycidonitrile with an alkanoyl halide having from 2 to 8 carbon atoms in the alkanoyl and the halide is chloride, bromide or iodide in the presence of a catalytic amount of a mineral acid salt of a tertiary amine, e.g., pyridine hydrochloride, to form the 2-alkanoyl-3-halopropionitrile,
2. treating the 2-alkanoyl-3-halopropionitrile from step (1) with a tertiary amine, e.g., with triethylamine, to form the enol acylate,
3. subjecting the enol acylate from step (2) to hydrolysis with an aqueous alkali metal base to form the salt of 2-(4'-isobutylphenyl)propionic acid, and
4. acidifying the salt from step (3) with a strong acid, e.g., with sulfuric acid, to form 2-(4'isobutylphenyl)propionic acid. In this preferred process for the production of a pharmaceutical grade carboxylic acid, it is desired to destroy cyanide ion in the mixture by adding at least a stoichiometric amount, preferably from 30 to 50 stoichiometric excess, relative to the cyanide ion content, of an alkali metal persulfate, e.g., sodium or ammonium persulfate or hypochlorite after the addition of the alkali metal hydroxide.

In a preferred variation of that process a cyanide ion destroying substance is added after the enol acylate is contacted with the aqueous alkali metal base to form the carboxylate salt. Examples of cyanide ion destroying substances which can be used include the economical alkali metal, alkaline earth metal and ammonium salts of persulfate and hypochlorite ions, e.g., the lithium, sodium, potassium, calcium, magnesium, strontium, barium persulfate and hypochlorite salts. Preferred salts for this purpose are the sodium or ammonium salts of persulfate and hypochlorite ions. A sufficient amount of the cyanide ion destroying substance is usually an amount which is at least, stoichiometrically equivalent to the cyanide content in the mixture. Usually an excess of persulfate or hypochlorite ion, in the range of 30 to 50 percent, relative to the cyanide ion content is used to remove as much of the cyanide ion content as is reasonably possible in the first batch depending upon the use intended for the carboxylic acid product of the process.

Any readily available, economical carboxylic acid halide (III) can be used in the first step for treating the glycidonitrile starting material, since neither the acyl nor the halide moieties appear in the final acid product. Thus, for reasons of ready availability, economy and ease of handing the lower aroyl halides such benzoyl halide, the methyl-substituted benzoyl halides such as p-toluoyl halides and the alkanoyl halides having from 1 to 18 carbon atoms, more preferably those from 2 to 18 carbon atoms, and other economical acyl halides are used. We prefer to use acetyl chloride or benzoyl chloride for this acylation-halogenation step.

The tertiary amines and amine salts which are used in catalytic amounts, say, 1 to 10 percent, based on the amount of the carboxylic acid halide, are preferably the amines or the economical mineral acid salts of pyridine, tris ($C_1$ to $C_4$ alkyl)amines such as trimethylamine, triethylamine, tripropylamine, tributylamine, lutidine, and the simple substituted variants of pyridine such as nicotinic acid, nicotinamide, and the like. The tertiaryamine can be used alone as the catalyst for this step of the process. However, we prefer to use a simple acid salt e.g., the hydrogen chloride, hydrogen bromide, hydrogen iodide salts of the tertiary amines to assist the hydrohalogenation part of the reaction. The acid which forms the salt with the tertiary amine is preferably complimentary to the acyl halide which is used. For example, if acetyl chloride is the selected acyl halide reactant a preferred tertiary amine salt catalyst for that reaction would be the hydrogen chloride salt of the tertiary amine. However, simple hydrogen halide-tertiary amine salts which are halide analogs to the selected acyl halide reactants, e.g., a triethylamine.hydrobromide salt catalyst combined with a propionyl chloride reactant can also be used. In that situation the 2-acyloxy-3-halopropionitrile (IV) may be a mixture of the 3-halo-compounds. However, this mixed halogen situation is not critical to the process since neither the halide nor the acyl group appear in the carboxylic acid product of the process.

In carrying out the improved process of this invention the selected glycidonitrile is placed in an appropriate reaction vessel, alone, or diluted with an appropriate substantially anhydrous solvent or diluent such as hexane mixtures, e.g., Skellysolve B, H or L, petroleum ethers, e.g., Skellysolve F and G, diethyl ether, xylene, toluene or the like, or mixtures thereof, and mixed with at least a stoichiometrically equivalent amount of the carboxylic acid halide in the presence of the catalytic amount of the tertiary amine or the tertiary amine acid salt. Since the glycidonitrile is usually the most expensive reactant and it is that reactant which is to be converted as completely as possible, an excess of the carboxylic acid halide is generally used to insure complete reaction of the glycidonitrile.

A catalytic amount of the tertiary amine or salt thereof is an amount which will promote the reaction of the glycidonitrile (II) with the carboxylic acid halide to effect both acylation and hydrohalogenation reactions of the glycidonitrile to form the 2-acyloxy-3-halopropionitrile intermediate.

To effect complete reaction the mixture is preferably stirred and maintained at any temperature ranging from about 0° C. to reflux temperature of the mixture, depending upon the speed of the reaction which is desired and the reactivity of the particular reagents involved. Generally, temperatures of from about 20° C. to about 80° C. are preferred for most combinations of reactants. In some cases the reaction is quite rapid but to insure complete reaction the reaction mixtures are generally stirred for from 1 hour or until an analysis of a sample of the reaction mixture indicates that no more glycidonitrile is present. Generally, the reaction is complete within 10 hours.

When the glycidonitrile reaction is completed the resulting 2-acyloxy-3-halopropionitrile (IV) containing reaction mixture is treated with a base, preferably a tertiary amine such as trimethylamine or triethylamine, or with a mixture of a catalytic amount of a trialkylamine and an economical alkali metal salt of a weak acid, such as sodium carbonate, potassium bicarbonate, or the like, to effect dehydrohalogenation of the 2-acyloxy-3-halopropionitrile to form the 2-acyloxy acrylonitrile (V) (enol-acylate) and to form the alkali metal halide and to regenerate the trialkylamine. This reaction is allowed to occur at a temperature sufficient to effect substantially complete dehydrohalogenation of the 2-acyloxy-3-halopropionitrile (IV) over a reasonable time, say in less than 24 hours. Temperatures ranging from 20° C. to the boiling point of the mixture can be used.

The 2-acyloxy-acrylonitrile derivative (V) (the enol-acylate) containing mixture can then be cooled, filtered to remove the base halide salt, and if desired, washed with an appropriate solvent such as toluene to further remove the enol-acylate intermediate solution.

The resulting enol-acylate reaction mixture is then treated with an aqueous alkali metal base such as aqueous sodium hydroxide to hydrolyze the enol acylate (V) to form the alkali-metal salt of the carboxylic acid (VI). Any alkali metal hydroxide may be used. However, it is preferred to use aqueous sodium, potassium or lithium hydroxide bases to effect good crystal formation of the carboxylic acid salt. To aid crystallization, we find it advantageous to seed the reaction mixture with crystals of the carboxylic acid salt.

After the aqueous base addition step the reaction mixture still contains cyanide ion which was expelled during the aqueous hydrolysis reaction. If desired at this time a cyanide ion destroying substance can be added in an amount sufficient to destroy that cyanide ion, without acting deleteriously on the carboxylic acid salt intermediate product in the reaction mixture. Compounds which are effective for this purpose are those described above. The economical sodium and ammonium salts of these ions are preferred. At least a stoichiometric amount of the cyanide ion destroying substance is generally used. A 30 to 50 molar percent excess of sodium or ammonium persulfate or hypochlorite ion generally effectively destroys substantially all of the cyanide ion in the mixture. Crystallization, redissolution and retreatment of the alkali metal carboxylate salt with the cyanide ion destroying substance can be done if extremely high purity is desired.

The carboxylic acid salt (VI) is then diluted in an appropriate organic or aqueous solvent system and acidified with an acid strong enough to dissolve and ionize the salt to form the free carboxylic acid (I). The acid used is preferably an economical mineral acid such as sulfuric or hydrochloric acid. The mixture can be stirred for a time sufficient to effect complete reaction of the salt to form the carboxylic acid. The by-product salt can be filtered, the carboxylic acid solution can be washed to remove soluble materials. The carboxylic acid product can be recovered from the reaction mixture by conventional methods. When the carboxylic acid product is a solid such methods can include drying the solution with sodium sulfate, decolorizing the solution with activated charcoal, seeding the solution with crystals of the carboxylic acid from other batches, and concentrating the mixture to volatilize solvents. When the acid product is a liquid, the reaction mixture can be distilled, under vacuum pressure, if necessary, or esterified by conventional methods and removed from the reaction mixture as the ester, and regenerated from the ester by conventional methods.

The process of the invention is further described and exemplified in the following detailed examples, but the examples are not intended to limit the scope of the invention.

Preparation A

A mixture of 17.6 g. of p-isobutylacetophenone (VII) and 61 ml. of a 15.4% w/v solution of chloroacetonitrile in xylene is cooled to about −10° C. and a solution of sodium t-amylate (prepared by stirring 4.45 g. of sodium amide and 10.0 g. of t-amyl alcohol in 150 ml. of xylene at 60° C. for about 4 hours) is added with stirring over a period of about 15 minutes keeping the temperature at about −5° C. Stirring is continued for an additional period of about 1 hour and then 70 ml. of water is added. The reaction mixture is then filtered and the organic (xylene) phase is separated. The aqueous layer is extracted with 30 ml. of xylene and the xylene solutions are combined, dried over anhydrous sodium sulfate and concentrated. The residue thus obtained is distilled (105° C./.05 mm.) to give 18.88 g. (88% yield) of 3-methyl-3-(p-isobutylphenyl)-glycidonitrile as an oil.

EXAMPLE 1

A. A batch of 3-methyl-3-(4'-isobutylphenyl)-glycidonitrile (II) (98.6 percent pure; 107.50 g.; 0.493 mole) prepared as described in Preparation A above was placed in a 1 liter three-necked flask equipped with a condenser and drying tube. Acetyl chloride (III) (technical, 44.3 ml.; 0.625 mole) and pyridine hydrochloride, (2.5 g.) were added and the resulting mixture was stirred at 50° C. for 2.5 to 3 hours. A thin layer chromatogram (TLC) analysis of a sample of the reaction mixture indicated that the 3-methyl-3-(4'-isobutylphenyl)glycidonitrile (II) starting material was gone. The solution contained mostly the 2-acetoxy-3-chloro-3-(4'-isobutylphenyl)propionitrile (IV) and some 2-hydroxy-3-chloro-3-(4'-isobutylphenyl)propionitrile. Toluene (375 ml.) and triethylamine (90.0 ml.; 0.690 mmoles) were added and the mixture was stirred at 110°–115° C. for 18 hours to effect dehydrohalogenation.

After that time analysis showed the reaction mixture still contained 2 to 3 percent unconverted chloroacetate or chloroalcohol, and about 82 percent of the enol-acetate, 2-acetoxy-3-(4'-isobutylphenyl)-3-methylacrylonitrile (V). The enol-acetate (V) containing mixture was allowed to cool to 25° C. and the triethylamine hydrochloride was filtered off and washed twice with 70 ml. portions of toluene. The filtrate weighted 554.1 g. and represents 0.493 mole of glycidonitrile starting material.

B. Hydrolysis of enol-ester followed by persulfate treatment to destroy cyanide.

A portion of the enol-acetate solution (V) from A above, (55.41 g. representing 49.3 mmole of enol-acetate) was placed in a 250 ml. 1 necked flask and stirred magnetically while 10 ml. of saturated sodium chloride solution and 16.0 g. of 50 percent sodium hydroxide solution (200 meq.) were added. The mixture was stirred and allowed to cool to 25° C. and the ammonium persulfate [$(NH_4)_2 S_2O_8$] (12.5 g.; 55 meq.) in 16 ml. of water were added over 10 minutes. After stirring overnight, 10 ml. of diglyme was added and the pH was adjusted from 9 to 13. The mixture was slowly cooled to 0° C. with seeding with crystals of 2-(4'-isobutylphenyl)propionic acid, sodium salt and held at 0° C. for 3 hours to form solid sodium 2-(4'-isobutylphenyl)propionate (VI) as a crystalline precipitate.

The solid crystalline precipitate was filtered (4 minutes on a coarse frit), washed with cold brine (8 ml. of saturated sodium chloride solution containing 3 ml. of ice) and then with 10 ml. of cold methylene chloride. The aqueous portion of the filtrate (60 ml.) showed 98 parts per million (ppm) of sodium cyanide. The cake was dried to give 15.56 g. yield of sodium 2-(4'-isobutylphenyl)-propionate.

A 1.0 g. portion of the dried cake was removed for assay; it showed 0 ppm. of sodium cyanide after distillation of HCN and colorimetric determination.

The remaining salt (14.56 g.) was slurried with water (the slurry gives negative picric paper test). Then 56 ml. of Skellysolve B (SSB- See Merck Index, 8th Edition, p. 951) and 8 ml. of 12 N sulfuric acid were added with warming to about 40° C. The mixture was filtered and phases of the filtrate separated. The upper phase was washed with 20 ml. of warm water. Both aqueous layers were back washed in sequence with a 20 ml. portion of SSB. The two SSB layers were then stirred with a mixture of sodium sulfate and 0.5 g. of decolorizing charcoal, (DARCO Brand) filtered through a filter aid (Celite brand) and concentrated to about 13 ml. The resulting acid solution was seeded with crystals of 2-(4'-isobutylphenyl)propionic acid and held to 0° C. for 2 hours. The 2-(4'-isobutylphenyl)propionic acid precipitate was filtered, washed with two 3 ml. portions of SSB and dried overnight at 50° C. The yield of 2-(4'-isobutylphenyl)propionic acid (I), based upon the 4-isobutylphenylglycidonitrile starting material, with correction for the removed portions of the sodium salt was 8.05 g. (79.4 percent). Thin layer chromatography (using ethyl acetate: benzene, concentrated ammonia: water; 55:39:3:3) shows no impurity. The mother liquor still contained 0.211 g. of the 2-(4'-isobutylphenyl)propionic acid.

EXAMPLE 2

A. The procedure to prepare the 2-acetoxy-3-(4'-isobutylphenyl)-3-methylacrylonitrile enol-acetate was as described in Example 1, part A.

B. Hydrolysis followed by hypochlorite treatment to destroy cyanide.

A. 55.41 g. portion of the crude enol-acetate solution from part A, representing 49.3 mmoles of 2-acetoxy-3-(4'-isobutylphenyl)-3-methylacrylonitrile (V) was placed in a 250 ml. one-necked flask and stirred magnetically while 10 ml. of water and 16.0 g. (200 meq.) of 50 percent sodium hydroxide solution were added. The mixture was stirred at 70° C. for 7 hours and cooled to 25° C. to effect hydrolysis of the enol-acetate and to form the sodium salt (VI). The ph of the mixture was adjusted to 11 with 12 percent sulfuric acid (3.5 ml.). Sodium hypochlorite solution (15 percent W/V, 30 meq.; 24.8 ml.) was added over 30 minutes with ice water cooling of the flask. Methylene chloride (10 ml.) and 0.8g. of a filter aid (Celite) were added and the mixture was slowly cooled to 0° C. After 3 hours the solids were filtered (3 minutes on a coarse frit) and washed with cold brine (8 ml. of saturated sodium chloride solution plus 3 ml. of ice) and with 10 ml. of cold methylene chloride. The cake was dried to give 9.68 g. A 1 gram sample was removed for cyanide assay; it showed 40 parts per million sodium cyanide. The remaining salt, 8.68 g. was slurried with water. The slurry gave a negative picric paper test, and then 56 ml. of Skellysolve B (SSB) and 8 ml. of 12 N sulfuric acid were added, with warming to 40° C. The mixture was filtered and phases were separated. The upper phase was washed with 20 ml. of warm water. The combined aqueous phase were back washed in sequence with a 20 ml. portion of SSB. The two SSB phases were then stirred with a mixture of sodium sulfate and decolorizing charcoal (0.5 g.), filtered through a filter aid and concentrated to about 15 ml. volume. The resulting acid solution was seeded with crystals of 2-(4'-isobutylphenyl)propionic acid and held at 0° C. for 2 hours. The resulting precipitate of 2-(4'-isobutylphenyl)propionic acid (1) was filtered, washed with two 3 ml. portions of cold SSB and dried overnight at 50° C. The yield of 2-(4'-isobutylphenyl)propionic acid, based upon the glycidonitrile starting material, with correction for removed analysis samples of the sodium salt was 8.00 g. (78.8 percent). A thin layer chromatogram analysis showed no impurity. The mother liquor still contained 0.120 g. of the acid (I).

EXAMPLE 3

Following generally the procedure of Example 1, 3-methyl-3-pentyl-glycidonitrile (II) is treated with propionoyl bromide (III) in the presence of a catalytic amount of triethylamine hydrobromide to form 2-propionoyloxy-3-bromo-3-methyl-3-pentylpropionitrile (IV). The propionitrile (IV) is treated with triethylamine to form the 2-propionoyloxy-3-methyl-3-pentylacrylonitrile (V) enolacylate. The enol-acylate (V) is treated with aqueous potassium hydroxide to form the potssium 2-methylheptanoate salt (VI). The reaction mixture is treated with potassium hypochlorite to destroy cyanide ion in the mixture. The potassium salt (VI) is removed from the reaction mixture and diluted with a Skellysolve B-water mixture and then treated with 12N sulfuric acid to form the 2-methylheptanoic acid. Such acid is useful for modifying starches. (U.S.S.R Patent 348,576; C.A., 78 31775 w.).

EXAMPLE 4

Following generally the procedure of Example 1, and using an epoxy nitrile, prepared by a Darzens condensation of benzaldehyde with chloroacetonitrile by the methods of Preparation A above, there is obtained phenylacetic acid as products of the process.

Thus, the process of this invention permits the halogenation and acylation to be done in one step, while permitting the avoidance of the necessity to use large quantities of pyridine. This process can also be run with more concentrated reaction mixtures than the above referenced hydrogen halide process.

I claim:

1. Process for the production of a carboxylic acid of the formula

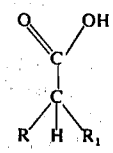

I wherein R, when taken separately, represents hydrogen or an aliphatic, alicyclic, aromatic or heterocyclic group and $R_1$ when taken separately, represents an aliphatic, alicyclic, aromatic or heterocyclic group, and R and $R_1$, when taken together and connected, represent an alicyclic or heterocyclic group, which comprises 1. treating a glycidonitrile of the formula

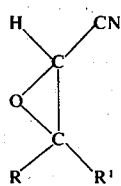

wherein R and R₁ have the meaning given hereinabove, with a carboxylic acid halide of the formula

wherein

denotes the carboxylic acyl group having from 1 to 18 carbon atoms and X is chlorine, bromine or iodine, in the presence of a tertiary amine or a tertiary amine acid salt in an amount and for a time sufficient to form a 2-acyloxy-3-halopropionitrile acylate of the formula

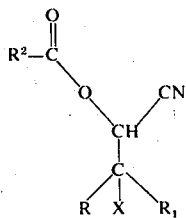

wherein R, R₁ and X are as defined above and

is the carboxylic acyl group;
2. dehydrohalogenating with a base the acylate from step (1) to form the enol acylate of the formula

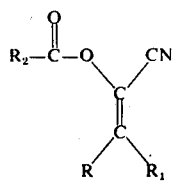

wherein R, R₁ and R₂ are as defined above;
3. subjecting the enol-acylate so obtained to hydrolysis with an aqueous alkali metal base to obtain an alkali metal salt of a carboxylic acid of the formula

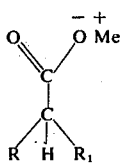

wherein R and R₁ have the meaning given above and Me is selected from the group consisting of sodium, potassium and lithium cations; and
4. acidifying the alkali metal salt of the carboxylic acid so obtained with a strong acid to obtain the corresponding free carboxylic acid (I).

2. Process according to claim 1 wherein a cyanide ion destroying amount of a substance selected from the group consisting of alkali metal, alkaline earth metal and ammonium salts of persulfate and hypochlorite ions is added to the reaction mixture after the step of contacting the enol acylate with the alkali metal base to form the alkali metal salt of the carboxylic acid.

3. Process according to claim 1 wherein the carboxylic acid halide used in step (1) is an alkanoyl halide having from 1 to 18 carbon atoms.

4. Process according to claim 1 wherein step (2) the 2-acyloxy-3-halopropionitrile enol acylate is dehydrohalogenated with a tertiary amine.

5. Process according to claim 1 wherein R is aromatic and R₁ is aliphatic.

6. Process according to claim 5 for preparing 2-(4'-isobutylphenyl)propionic acid which comprises;

1. treating 3-methyl-3-(4'-isobutylphenyl)glycidonitrile with an alkanoyl halide having from 2 to 18 carbon atoms in the alkanoyl group and the halide is chloride, bromide or iodide, in the presence of a catalytic amount of a tertiary amine or a mineral acid salt of a tertiary amine to form the 2-alkanoyloxy-3-halopropionitrile;
2. treating the 2-alkanoyloxy-3-halopropionitrile from step (1) with a tertiary amine to form the enolacylate;
3. subjecting the enol acylate from step (2) to hydrolysis with an aqueous alkali metal base to obtain an alkali metal salt of 2-(4'-isobutylphenyl)propionic acid, and;
4. acidifying the salt with a strong acid to form 2-(4'-isobutyl)phenylpropionic acid.

7. Process according to claim 6 wherein, 1. 3-methyl-3-(4'-isobutylphenyl)glycidonitrile is treated with acetyl chloride in the presence of a catalytic amount of pyridine hydrochloride to form a mixture containing 2-acetoxy-3-chloro-3-(4'-isobutylphenyl)-3-methylpropionitrile,
2. the 2-acetoxy-3-chloro-3-(4'-isobutylphenyl)-3-methylpropionitrile containing mixture is treated with a tri(C₁to C₄ alkyl)amine to form 2-acetoxy-3-(4'-isobutylphenyl)-3-methylacrylonitrile,
3. the enol acetate from step (2) is treated with an aqueous sodium hydroxide to form the sodium 2-(4'-isobutylphenyl)propionate salt, and
4. the salt from step (3) is treated with sulfuric acid to form 2-(4'-isobutylphenyl)propionic acid.

8. Process according to claim 7 wherein an alkali metal or ammonium persulfate salt is added to the reaction mixture after the addition of the sodium hydroxide in an amount sufficient to destroy cyanide in the mixture.

9. Process according to claim 7 wherein an alkali metal or ammonium hypochlorite is added to the reaction mixture after the addition of the sodium hydroxide in an amount sufficient to destroy cyanide in the mixture.

10. In a process for preparing a carboxylic acid of the formula

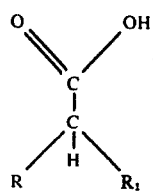 I wherein R, when taken separately, represents hydrogen or an aliphatic, alicyclic, aromatic or heterocyclic group and R , when taken separately, represents an aliphatic, alicyclic, aromatic or heterocyclic group, and R and R , when taken together and connected, represent an alicyclic or heterocyclic group, from a glycidonitrile of the formula

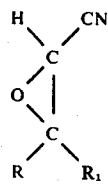 II wherein R and R have the meaning given hereinabove, the improvement which comprises 1. treating the glycidonitrile of formula II above with a carboxylic acid halide of the formula

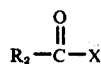 III wherein R —C(O)—denotes the carboxylic acyl group having from 1 to 18 carbon atoms, and X is chlorine, bromine or iodine, in the presence of an acid salt of a tertiary amine in an amount and for a time sufficient to form a 2-acyloxy-3-halopropionitrile acylate of the formula

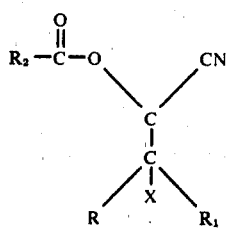 IV wherein R, R and X are as defined above and R C(O)- is the residue of the carboxylic acyl group;

2. dehydrohalogenating the halo-acylate IV from step (1) with a base to form the acylated acrylonitrile enol acylate of the formula

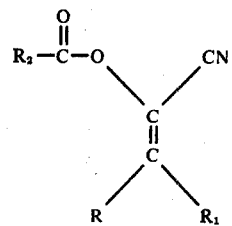 V wherein R, R and R are as defined above;

3. hydrolyzing the enol-acylate V from step (2) with an aqueous alkali metal base to form an alkali metal salt of a carboxylic acid of the formula

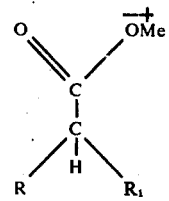 VI wherein R and R are as defined above and $\overset{+}{Me}$ is the alkali metal cation from the base, and 4. acidifying the alkali metal salt of the carboxylic acid from step (3) with an acid strong enough to form the corresponding free carboxylic acid (1).

11. An improved process in accordance with claim 10 wherein R is aromatic and R is aliphatic.

12. An improved process in accordance with claim 10 which further includes the step of adding a cyanide ion destroying amount of an alkali metal, alkaline earth metal or ammonium salt of persulfate or hypochlorite ions after the aqueous alkali metal base is added to the enol acylate to form the alkali metal salt of the carboxylic acid.

13. An improved process in accordance with claim 10 for making 2-(4 -isobutylphenyl)propionic acid wherein in step (1) 3-methyl-3-(4 -isobutylphenyl)-glycidonitrile is reacted with an alkanoyl halide having from 2 to 18 carbon atoms in the alkanoyl group and the halide is chloride, bromide or iodide, in the presence of a catalytic amount of a mineral acid salt of a tertiary amine to form the 2-alkanoyloxy-3-halopropionitrile, in step (2) the 2-alkanoyloxy-3-halopropionitrile from step (1) is treated with a tertiary amine to form the enol-acylate, in step (3) the enol acylate from step (2) is subjected to hydrolysis with an aqueous alkali metal hydroxide to form the salt of 2-(4 -isobutylphenyl)-propionic acid, and in step (4) the salt from step (3) is acidified to form 2-(4 -isobutylphenyl)propionic acid.

* * * * *

UNITED STATES PATENT OFFICE
CERTIFICATE OF CORRECTION

Patent No. 3,987,094     Dated  October 19, 1976

Inventor(s)  David R. White

It is certified that error appears in the above-identified patent and that said Letters Patent are hereby corrected as shown below:

Column 13, line 15, claim 10, "R " should read --$R_1$--; line 17, claim 10, "R and R " should read --R and $R_1$--; line 30, claim 10, "R and R " should read --R and $R_1$--; line 39, claim 10, "R -C(O)-" should read -- $R_2$-C(O)- --; line 57, claim 10, "R, R and" should read --R, $R_1$ and--; line 57, claim 10, "R C(O)-" should read -- $R_2$C(O)- --; Column 14, line 15, claim 10, "R, R and R are" should read --R, $R_1$ and $R_2$ are--; line 29, claim 10, "R and R " should read --R and $R_1$--; line 34, claim 11, "and R is aliphatic" should read --and $R_1$ is aliphatic-- .

Signed and Sealed this

Fifteenth Day of March 1977

[SEAL]

Attest:

RUTH C. MASON
*Attesting Officer*

C. MARSHALL DANN
*Commissioner of Patents and Trademarks*